United States Patent [19]

Dunegan

[11] Patent Number: 5,014,556
[45] Date of Patent: May 14, 1991

[54] ACOUSTIC EMISSION SIMULATOR

[75] Inventor: Harold L. Dunegan, Laguna Niguel, Calif.

[73] Assignee: Dunegan Engineering Consultants, Inc., Irvine, Calif.

[21] Appl. No.: 465,481

[22] Filed: Jan. 16, 1990

[51] Int. Cl.$^5$ .............................................. G01N 29/00
[52] U.S. Cl. .................................... 73/587; 73/1 DV
[58] Field of Search ...................... 73/801, 587, 865.6, 73/1 DV

[56] References Cited

U.S. PATENT DOCUMENTS

| | | |
|---|---|---|
| 3,529,465 | 9/1970 | Kleesattel et al. |
| 3,774,443 | 11/1973 | Green et al. |
| 3,979,949 | 9/1976 | Smith |
| 4,018,084 | 4/1977 | Hsu .......................................... 73/801 |
| 4,064,735 | 12/1977 | Hutchison et al. ............... 73/801 X |
| 4,107,980 | 8/1978 | Crane et al. |
| 4,188,830 | 2/1980 | Mason et al. ......................... 73/801 |
| 4,409,841 | 10/1983 | Archer ................................ 73/762 |
| 4,584,879 | 4/1986 | Webster et al. ...................... 73/588 |

Primary Examiner—Jerry W. Myracle
Attorney, Agent, or Firm—Martens, Olson & Bear Knobbe

[57] ABSTRACT

The invention simulates acoustic emission signals produced by crack growth within a structure so that listening equipment may properly be calibrated to listen for acoustic emission signals from actual structural crack growth. The invention has several embodiments which generate acoustic emission signals from a crack growing in a specimen such that the acoustic emission signals have a broad bandwidth as the crack grows. The acoustic emission signals produced by the growing crack can be introduced into a structure being monitored through a cone-shaped portion which is bonded to the structure being monitored.

17 Claims, 4 Drawing Sheets $N = AK^\eta$

ACOUSTIC EMISSION SIMULATOR

BACKGROUND OF THE INVENTION

1. Field of the Invention

The present invention relates to devices which simulate the failure of materials used in structures so that failure can be predicted. More particularly, the invention relates to devices using acoustic emission techniques for simulating failure.

2. Description of the Related Art

Structures such as bridges, buildings and aircraft are constantly subjected to high stresses and corrosion. Structures can fail because of high stress and corrosion. Structural failure occurs when cracks develop and grow in a structure due to stress. Prediction of structural failure is desirable since it can save lives and property. However, prediction of structural failure is not easy. One cannot always tell from looking at a structure whether a structure is prone to failure. Often, a structure cannot be viewed because it is hidden, such as the structure of a concrete building or an airplane.

Structural failure could be predicted by removing a portion of a structure and testing the portion removed. This kind of method is known as a destructive testing method. Such a method, however, is impractical since the removal of a sample from a structure would further weaken the structure.

Because of the impracticality of destructive testing methods, nondestructive testing methods have been developed. One widely used nondestructive testing method which is very reliable is the use of acoustic emission technology. Acoustic emission technology is based on the fact that when a crack in a structure propagates, it produces an acoustic emission. If these emissions can be detected, the damage to a structure can be measured. Thus, acoustic emission technology can be used to predict structural failure.

Acoustic emission techniques involve attaching high frequency ultrasonic transducers (20 Khz–500 Khz) to a structure under stress to listen for the high frequency sound waves released when a crack propagates in the structure. In order for acoustic emission monitoring to be effective, especially when continuously monitoring a structure, it is necessary to assure that the signal due to propagation of the crack can be distinguished from background noise which is always present during operation. Additionally, it is necessary to determine the attenuation of crack-like acoustic emission signals within the structure in order to determine what spacing to use for the transducers in order to assure that complete coverage of the structure is accomplished. Finally, it is necessary to determine if a proper failure model is present in the system software to predict that failure of the structure is imminent, so that it can be unloaded prior to catastrophic failure. These requirements can be easily accomplished by simulating actual acoustic emission signals from a crack while monitoring the structure for the simulated signals.

The main factor hindering the application of acoustic emission techniques to the testing of critical structures is the lack of a simulated signal source with the required bandwidth to simulate the growth of a crack in a critical structure. One method for simulating the required bandwidth involves placing a transducer similar to the transducer being used to detect the acoustic emission signals from crack growth on the structure and pulsing the transducer with a step voltage pulse. This causes the transducer to send out an artificial acoustic emission signal throughout the structure. The problem with this technique is that the frequency content of the signal sent out is a very narrow band centered around the resonant frequency of the sending transducer, unlike a wide band signal from a growing crack.

Another method for simulating the required bandwidth is the use of a pencil, where a small piece of pencil lead is broken when the pencil is pressed against the structure. This technique more closely simulates the signal from a growing crack but it is very awkward to use, and is impossible to use in many situations involving real structures.

SUMMARY OF THE INVENTION

The preferred embodiment of the present invention uses a weakened bolt in which crack growth is created. The other parts of the invention are reusable, so only the bolt needs to be replaced in order to reuse the device.

The present invention also has the advantage of being compact, lightweight and simple to use.

The preferred embodiment of the present invention comprises the combination of a waveguide, a body, a bolt, and a cap. The waveguide is cone-shaped to simulate a point source of acoustic emission signals and is attached to the structure to be monitored. The body mates the waveguide and the bolt together. The bolt is hydrogen charged and is stressed across a machined groove by tightening the bolt into the body. The acoustic emission signals produced by the crack propagation in the machined groove of the bolt are transmitted into the structure by the waveguide. A cap covers the head of the bolt and contains the head of the bolt after bolt failure.

The present invention has the advantage of accurately simulating the acoustic emission signals which emanate from a crack growing in a structure so that monitoring equipment may be effectively calibrated for monitoring the structure and predicting failure. Thus, the present invention simulates the acoustic emission signals as if they emanated from a point source, which is what happens with actual crack growth in a structure.

This significant advantage is accomplished by a compact, lightweight device which is simple to use. Moreover, in the preferred embodiment, all parts of the invention are reusable with the exception of the weakened grooved bolt. Replacement of this bolt is simple and permits immediate reuse of the device.

Another feature of the preferred embodiment of the present invention is that the body contains a plurality of fins which provide several advantages. The first advantage is that the fins absorb and scatter any stress waves that couple into the body through the screw threads of the bolt. The second advantage is that the fins minimize reflections from the head of the bolt back into the body and the setting up of standing waves in the body. The third advantage is that the fins provide a heat sink, which allows the waveguide to be attached to a hot structure without seriously affecting the performance of the bolt.

A feature of another embodiment of the present invention is that a specimen contains screw threads cut along the exterior surfaces and the specimen is encapsulated in a metal loaded urethane containing entrapped air bubbles. Loading the urethane with Tungsten powder helps to acoustically match the impedance at the surface to cause the stress waves to enter the mixture. The entrapped air in the urethane absorbs the energy of the stress waves to prevent them from being reflected back into the device. The screw threads prevent phase coherent reflections from occurring as well as help to provide a surface for entry of the stress waves into the urethane mixture.

Both of the embodiments of the present invention thus have features which have the advantage of minimizing multiple internal reflections. Such multiple internal reflections are disadvantageous because they tend to make the stress wave from a growing crack appear to be longer in time.

DETAILED DESCRIPTION OF THE PREFERRED EMBODIMENT

Figure 1:
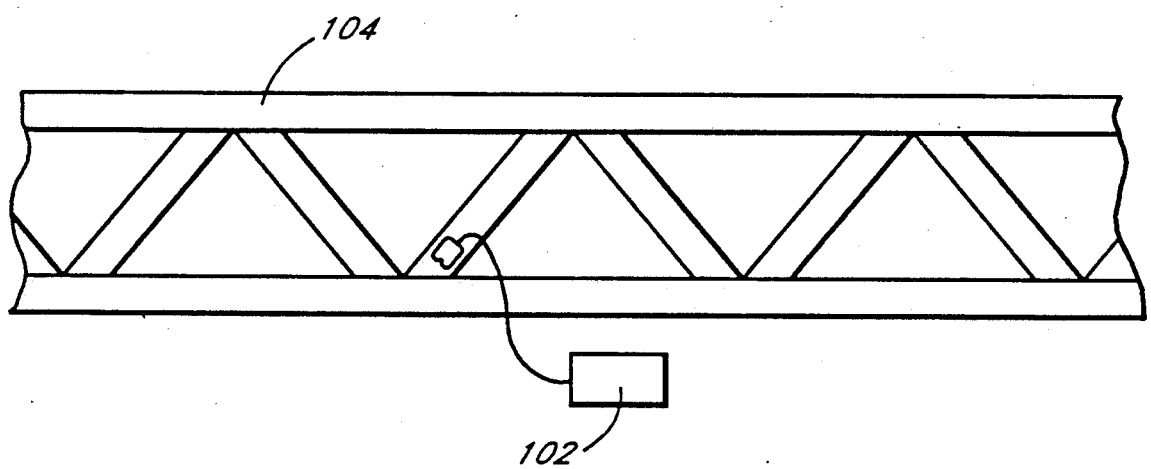
FIG. 1 illustrates an exemplary use of a transducer to monitor a structure for acoustic emission signals.

It is known that a crack in a structure produces acoustic emission signals as it grows. If these signals can be detected in a structure, then possible failure of the structure can be predicted. FIG. 1 illustrates a transducer 102 for monitoring for acoustic emissions. The transducer is shown connected to a bridge structure 104 for monitoring acoustic emission signals generated by cracks in the structure 104.

In order for monitoring equipment to be properly tuned to acoustic emission signals generated in a particular structure, it is necessary to simulate representative acoustic emission signals. A method for simulating acoustic emission signals in a structure, which is preferred because of its accurate simulation, is propagating a crack within a specimen attached to the structure. In this way, acoustic emission signals identical to those which would be produced in a structure are injected into the structure so that monitoring equipment may properly be set up to detect actual acoustic emission signals and determine the possibility of failure or the location of significant damage in the structure.

Hydrogen charged specimens used to create crack growth while being monitored with acoustic emission transducers are known in the art. Hydrogen diffuses into a specimen during a common plating process, such as Cadmium plating. When a stress forms in the specimen, hydrogen diffuses to the stress and promotes the propagation of a crack.

Figure 2:
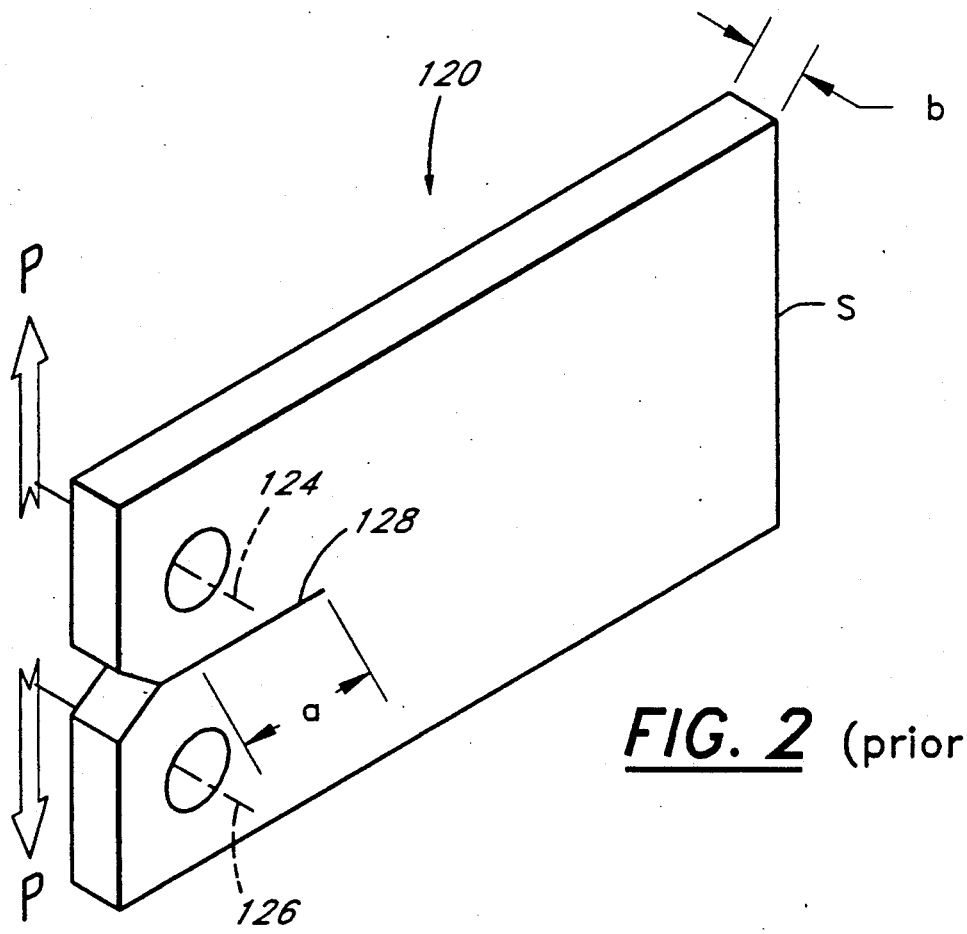
FIG. 2 is a hydrogen charged beam specimen useful for generating representative acoustic emission signals.

FIG. 2 illustrates a prior art specimen 120 used for the study of crack growth in materials due to hydrogen embrittlement and stress corrosion cracking. The specimen 120 is provided with holes 124, 126 for pin loading the specimen. The specimen is hydrogen charged and has a crack 128. The crack 128 has a length a. The specimen 120 has a width b. The surface S of the specimen 120 could be bonded to a structure so that the acoustic emission signals produced by the propagation of the crack 128 are injected into the structure. A load is placed on the specimen 120 by pulling in the direction indicated in FIG. 2 by an amount of force P. The loading causes the crack 128 to grow and to generate acoustic emission signals representing crack propagation. The monitoring equipment set up at another location on the structure could be then adjusted to pick up the acoustic emission signals generated by the specimen 120.

Figure 3:
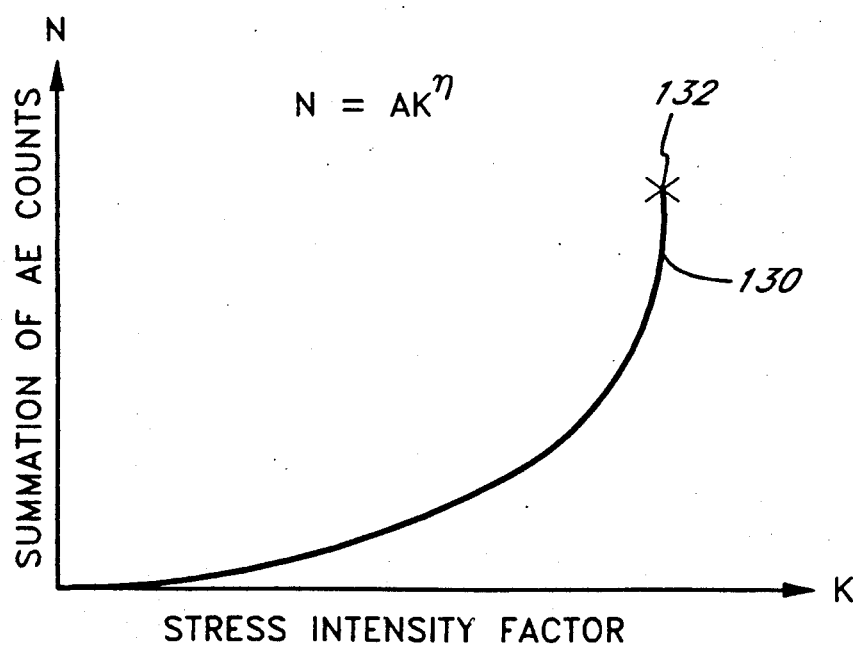
FIG. 3 is a graph showing the summation of acoustic emission (AE) counts as a function of the stress intensity factor K.

Acoustic emission signals have been shown to be related to the stress intensity factor K at the tip of a crack through a power function. This relationship is illustrated by the graph 130 shown in FIG. 3. The point 132 indicates the point at which failure occurs. The summation of acoustic emission (AE) counts as a function of the stress intensity factor K can be expressed as:

$$N = AK^\eta \tag{1}$$

Where
  N = Summation of acoustic emission counts
  A = Constant depending on geometry
  K = Stress intensity factor
  $\eta$ = An exponent related to the toughness of the material Since the stress intensity factor, K, is the controlling parameter for the stresses in the vicinity of a crack, and the critical value of K (called $K_c$, or the fracture toughness, which is a known value for the material) is where failure will occur, failure of a structure can easily be predicted if one can estimate, from acoustic emission monitoring of a structure, the value of K for the defects in the structure.

The equation relating the stress intensity factor K to the geometry of the specimen 120 shown in FIG. 2 can be expressed by:

$$K = P \sqrt{\frac{E}{2b} \cdot \frac{dC}{da}} \tag{2}$$

Figure 4:
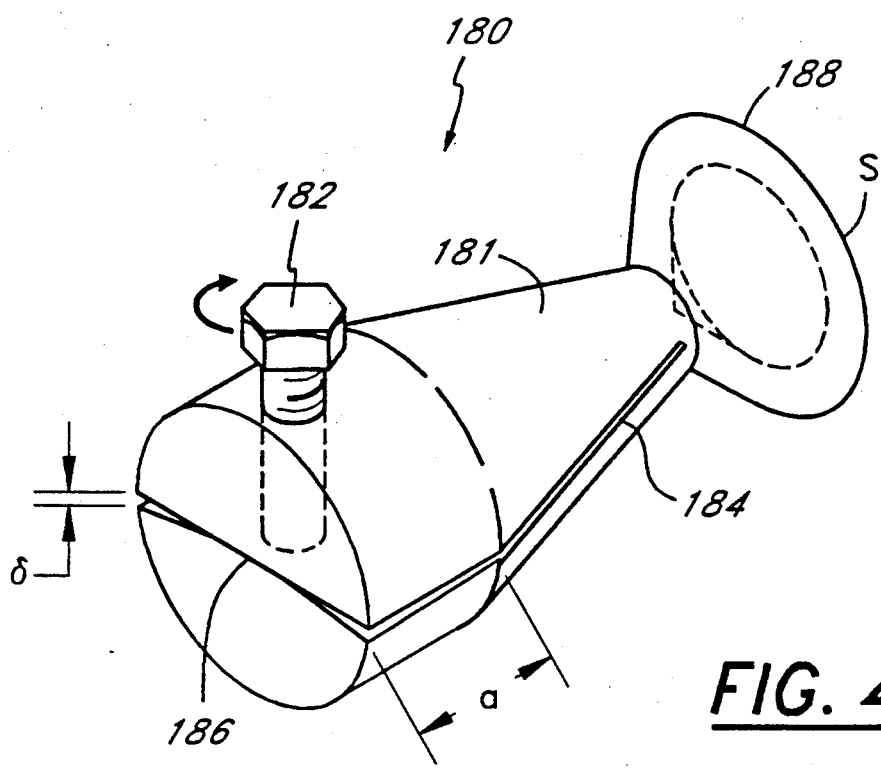
FIG. 4 is one embodiment of the present invention in which a bolt is used to load the specimen.

Where
  K = Stress intensity factor
  P = Load
  E = Youngs modulus for the material
  b = Thickness
  a = Crack length
  C = Compliance of the beams of the specimen FIG. 4 shows one embodiment of the present invention. The embodiment shown in FIG. 4 utilizes a constant displacement $\delta$ of a crack, rather than a constant load as in FIG. 2. Under constant displacement, the load causing the crack to grow will decrease as the crack grows longer. In order to assure that failure will occur, the compliance with respect to the crack length must increase faster than the load decreases in order for the specimen to go to failure. Therefore, the beams must be made more compliant as the crack grows. The embodiment in FIG. 4 accomplishes this.

The embodiment in FIG. 4 consists of a specimen 180 which has a beam section 181 that tapers from a larger circular cross-section to a smaller cross-section. A bolt 182 is used to load the specimen 180. The bolt 182 is turned so that a crack 186 has a displacement $\delta$. A side groove 184 assures that the crack 186 remains in a plane bisecting the specimen 180.

One problem with the device of FIG. 2 is that when the specimen 120 is attached to the structure, the specimen does not closely simulate acoustic emission signals coming from a point source in a structure. Simulation of a point source in a structure is most desirable because it is a better simulation of actual crack growth within a structure. In other words, the energy should be irradiated uniformly in all directions from the source.

The specimen 180 in FIG. 4 has the advantage of simulating acoustic emission signals from a point source. To accomplish this, the specimen 180 has a cone 188 at the end away from the bolt 182. A portion of the center of the cone 188 is removed. The surface S of the end of the cone 188 is attached to the structure. The cone 188 is designed such that stress waves created by crack growth, after passing through the reduced section, spread out uniformly and are injected into the structure at a 45 degree angle. Mode conversion of the stress waves injected in this manner will quickly cause most of the energy of the wave to take the form of a surface wave or lamb wave, depending on the thickness of the material of the structure. These wave types represent the type of waves encountered in practice from structures containing growing cracks.

In practice, the specimen 180 is loaded by turning the bolt 182 to a given displacement δ. The time to failure can be adjusted by using more or less displacement when the bolt 182 is initially loaded.

The surface S of the specimen 180 is attached to the structure with an epoxy cement, or by using magnetic hold-downs. In the latter configuration, the specimen 180 is magnetized and a coupling material (such as oil, silicone grease or other materials commonly used for this purpose) is placed upon the surface S prior to attachment to the structure under test.

Figure 5:
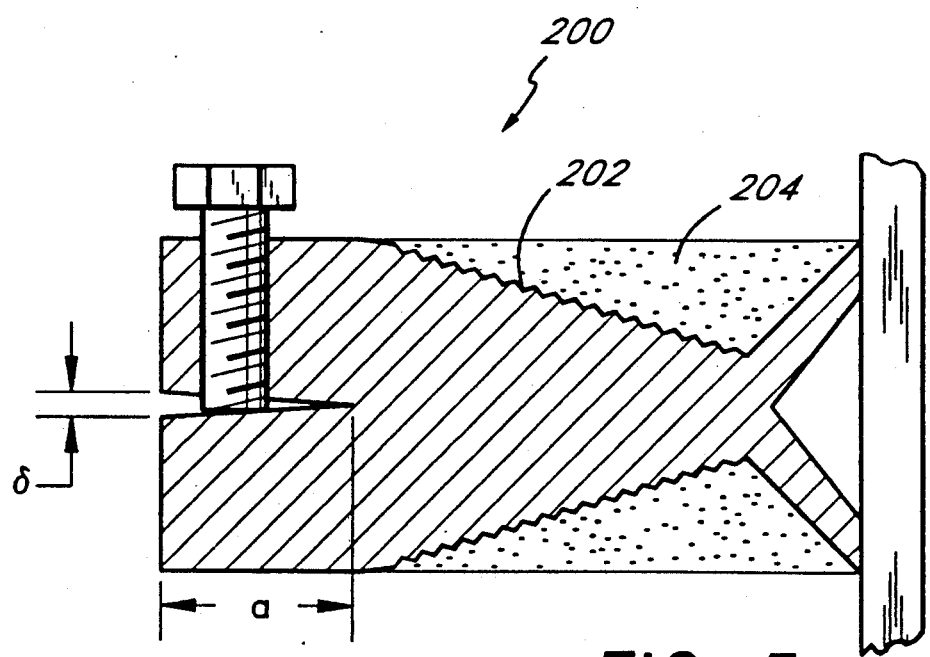
FIG. 5 is an alternative specimen design which is another embodiment of the present invention.
Figure 6:
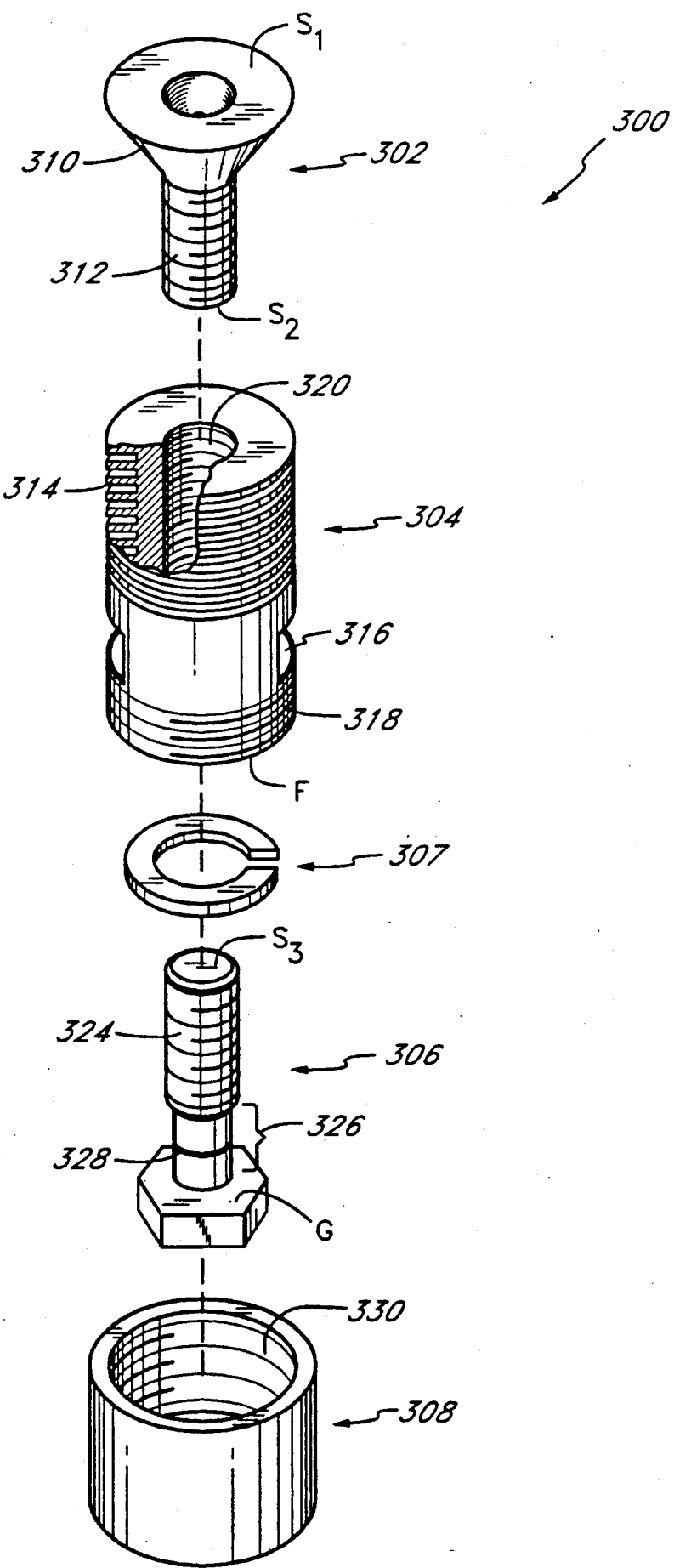
FIG. 6 is a device which is the preferred embodiment of the present invention.

FIG. 5 illustrates an alternative specimen design which is another embodiment of the present invention. The specimen 200 in FIG. 5 is similar to the specimen 180 shown in FIG. 4 with the additional features that screw threads 202 are cut along the exterior surfaces and the device is encapsulated in a metal loaded urethane 204 containing entrapped air bubbles. A significant feature of this embodiment and the preferred embodiment of FIG. 6 is that its design minimizes multiple internal reflections. Such multiple internal reflections are disadvantageous because they tend to make the stress wave from a growing crack appear to be longer in time. Loading the urethane with Tungsten powder will help to acoustically match the impedance at the surface to cause the stress waves to enter the mixture. The entrapped air in the urethane will absorb the energy of the stress waves to prevent them from being reflected back into the device. The screw threads will prevent phase coherent reflections from occurring as well as help to provide a surface for entry of the stress waves into the urethane mixture.

An expanded view of another embodiment of the present invention, the preferred embodiment, is shown in a device 300 in FIG. 6. The device 300 comprises four major components: a waveguide 302, a body 304, a bolt 306, a washer 307, and a cap 308. The waveguide 302 comprises a cone portion 310 and a threaded portion 312. The inside of the cone portion 310 is removed. The cone portion 310 is angled at 45 degrees from the center axis of the cone. The waveguide 302 is made of stainless steel.

The body 304 is also made of stainless steel. The body has plural outwardly radiating fins 314. The body 304 additionally comprises a flat portion 316 adapted to receive a wrench. Further, the body 304 comprises a threaded portion 318. The body 304 contains a threaded hole 320. The hole 320 is adapted to receive the threaded portion 312 of the waveguide 304 and the threads of the bolt 306.

The bolt 306 is a hydrogen charged bolt containing a stress concentration where a crack will form when the bolt 306 is stressed. The bolt 306 is preferably made of 4340 steel. The bolt 306 has a threaded portion 324 and a neck portion 326. The neck portion 326 contains a sharp groove 328 which is preferably 0.025 inches deep. The groove 328 is the stress concentration where a crack will form when the bolt 306 is stressed.

The washer 307 is preferably a load washer designed to prevent bolt from unloading.

The inside of the cap 308 contains threads 330 which are adapted to receive the threaded portion 318 of the body 304.

The surface $S_1$ of the cone portion 310 is attached to the structure to be monitored.

In practice, the bolt 306 is screwed into the body 306 through the washer 307 that contacts the surface F of the body 304 and surface G of the bolt 306 until the desired load is obtained. The waveguide 302 is then screwed into the body 304 until the flat surface $S_2$ of the waveguide 302 and the flat surface $S_3$ of the bolt 306 come into contact. The purpose of the washer 307 is to maintain the load once the crack starts in the bolt to assure that the bolt will be caused to go to failure instead of unloading. The purpose of the cap 308 is to capture the bolt head when the bolt fails and to provide environmental protection.

Advantageously, the waveguide 302, the body 304, the washer 307, and the cap 308 are reusable. If the waveguide 302 is attached to the structure by gluing, the waveguide may still be removed for reuse since it is strong enough to withstand the force needed in order to remove it.

The fins 314 of the body 304 serve several purposes. One purpose is to absorb and scatter any stress waves that couple into the body 304 through the screw threads 324 of the bolt 306. A second purpose is to minimize internal reflections and the setting up of standing waves. A third purpose is to provide a heat sink, which will allow the waveguide 302 to be attached to a hot structure without seriously affecting the performance of the hydrogen charged bolt 306. When assembled, the surface $S_2$ of the waveguide 302 and the surface $S_3$ of the bolt 306 will be in contact. A small amount of liquid coupling material is placed on each surface before assembly in order to assure that stress waves from the cracking of the bolt 306 will propagate across this interface into the waveguide 302 and subsequently into the structure to which the waveguide 302 is attached.

The amount of load put on the bolt 306 prior to it bottoming out of the washer 307 can be changed by using different washers or by using several washers in parallel or series and varying the initial torque used to load the bolt. The amount of load will determine the time required for the crack to begin to propagate as well as the total time to failure. The time to failure is also influenced by the yield strength of the bolt and the hydrogen concentration.

By way of specific example, the dimensions for a device constructed in accordance with the device 300 shown in FIG. 6 are as follows: The surface $S_1$ of the cone portion 310 has an outer diameter of 1.375 inches and an inner diameter of 0.625 inches. The waveguide 310 is 1.250 inches in length and the threaded portion 312 is 0.625 inches in length. The threads in the threaded portion 312 are ½-20. The length of the waveguide can be varied over a wide range without seriously affecting its performance.

The body 304 is 2.00 inches long and the fins 314 cover 1.00 inches of the body 304. The fins 314 are θ inch deep and are spaced 1/16 inches apart. The flat portion 316 is 0.375 inches long, 1/16 inches deep, and starts 0.375 inches from the surface F. The threaded portion 318 is 0.375 inches long and contains 1-⅜-20 threads.

The bolt 306 is 1.625 inches long, excluding the head. The threaded portion 324 is 1.125 inches long and comprises ½-20 threads. The neck portion 326 is 0.425 inches in diameter.

The cap 308 is 0.813 inches long and 1.500 inches in diameter. The threads 330 are 1-⅜-20.

What is claimed is:

1. An apparatus for simulating a point source of acoustic emission signals into a structure undergoing a nondestructive test comprising:
    a waveguide for attachment to said structure, said waveguide having a conical configuration to simulate a point source of acoustic emission signals,
    a hydrogen charged bolt having a machined groove about its axis for providing a hydrogen charged specimen in which a crack may be induced under torque; and
    a body having a mating threaded opening for holding the end face of said bolt in abutting contact with said waveguide so that as the bolt is rotated relative to said housing, the torque will induce a crack at said machined groove.

2. The apparatus of claim 1 wherein said body has a plurality of outwardly radiating fins for absorbing any stress waves that couple into said body through the screw threads of said bolt and for providing a heat sink for any excess heat energy induced into said apparatus by said structure under test and for absorbing internal reflections which tend to make the stress wave from a growing crack appear to be longer in time.

3. The apparatus of claim 1, wherein a loading washer is placed between the head of said bolt and said body to maintain the torque load upon the crack once this crack starts in the bolt to assure that the bolt will be caused to go to failure.

4. An apparatus for simulating a point source of stress waves in a structure undergoing nondestructive test, comprising:
    a specimen containing a crack portion adapted for containing a crack which grows, generating acoustic emission signals, when the specimen is loaded;
    a waveguide for attaching to said structure and injecting acoustic emission signals into said structure, said waveguide comprising:
        a cone portion for attaching to said structure, said cone portion having a conical shape so as to simulate a point source of acoustic emission signals; and
        a shank portion integral with said cone portion; and
    a body portion for receiving the shank portion of said waveguide and holding together said waveguide and said specimen, such that stress waves produced by said specimen are transferred to said waveguide.

5. The apparatus of claim 4, wherein said shank portion has threads.

6. The apparatus of claim 4, wherein said body portion has a threaded center hole.

7. The apparatus of claim 4, wherein said body portion has fins.

8. The apparatus of claim 4, wherein said body portion has a flat portion adapted to receive a wrench.

9. The apparatus of claim 4, wherein said specimen is a bolt.

10. The apparatus of claim 9, wherein said bolt contains a machined groove about its axis.

11. The apparatus as defined in claim 9, additionally comprising:
    a washer, said washer provided between said body portion and said bolt.

12. An apparatus as defined in claim 4, additionally comprising:
    a cap for encasing said specimen, said cap being attachable to said body portion.

13. A method of acoustic emission simulation in a structure, comprising:
    a. attaching a specimen and a waveguide to a body portion, said body portion comprising means for joining said specimen with said waveguide such that emissions from said specimen caused by propagation of a crack in said specimen are transferred to said waveguide;
    b. attaching said waveguide to a structure; and
    c. providing a load on said specimen such that said stress propagates a crack within said specimen.

14. An apparatus for simulating stress waves in a structure, comprising:
    a cone portion for attaching to said structure and injecting stress waves into said structure, said cone portion having a conical shape;
    a central portion integral with said cone portion, said central portion having a circular cross section, said circular cross section tapering to its narrowest at said cone portion, said central portion having oppositely placed longitudinal grooves on its surface;
    an end portion integral with said central portion, said end portion having a uniform circular cross section throughout, said end portion having oppositely placed longitudinal grooves on its surface integral with said longitudinal grooves of said central portion, said end portion having a crack lying in the plane of said longitudinal grooves; and
    a bolt, said bolt being inside a threaded hole of said end portion and extending through to said crack of said end portion and pressing against an opposite side of said crack.

15. The apparatus of claim 14, wherein said central portion has screw threads cut on its exterior surface and said central portion is encapsulated in a metal loaded urethane containing entrapped air bubbles.

16. An apparatus for simulating a point source of acoustic emission signals into a structure undergoing a nondestructive test, comprising:
    a waveguide for attachment to said structure, said waveguide simulating a point source of acoustic emission signals;
    a hydrogen charged specimen comprising a threaded bolt engaging said waveguide, said bolt having a weakened portion in which a crack will be induced when the bolt is placed under torque; and
    means for absorbing and minimizing stress waves that do not directly couple into said waveguide from said induced crack.

17. An apparatus for simulating a point source of acoustic emission signals into a structure undergoing a nondestructive test, comprising:
    a waveguide for attachment to said structure, said waveguide simulating a point source of acoustic emission signals; and
    a hydrogen charged specimen comprising a threaded bolt engaging said waveguide, such bolt having a weakened portion in which a crack will be induced when the bolt is placed under torque.

* * * * *